(12) United States Patent
Star-Lack et al.

(10) Patent No.: US 11,348,755 B2
(45) Date of Patent: May 31, 2022

(54) RADIATION ANODE TARGET SYSTEMS AND METHODS

(71) Applicant: Varian Medical Systems, Inc., Palo Alto, CA (US)

(72) Inventors: Josh Star-Lack, Palo Alto, CA (US); James Clayton, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 62 days.

(21) Appl. No.: 17/061,233

(22) Filed: Oct. 1, 2020

(65) Prior Publication Data

US 2021/0027973 A1 Jan. 28, 2021

Related U.S. Application Data

(63) Continuation of application No. 16/045,598, filed on Jul. 25, 2018, now Pat. No. 10,910,188.

(51) Int. Cl.
*H01J 35/00* (2006.01)
*H01J 35/08* (2006.01)
(Continued)

(52) U.S. Cl.
CPC ............ *H01J 35/08* (2013.01); *A61N 5/1065* (2013.01); *H01J 35/18* (2013.01);
(Continued)

(58) Field of Classification Search
CPC .......... A61N 5/00; A61N 5/10; A61N 5/1065; A61N 5/1077; H01J 35/08
See application file for complete search history.

(56) References Cited

U.S. PATENT DOCUMENTS

| 4,163,901 A | 8/1979 | Azam |
| 4,914,681 A | 4/1990 | Klingenbeck et al. |

(Continued)

FOREIGN PATENT DOCUMENTS

| CN | 104001270 | 8/2014 |
| CN | 106730407 | 5/2017 |

(Continued)

OTHER PUBLICATIONS

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/S41598-020-65819-y.

(Continued)

*Primary Examiner* — Dani Fox

(57) ABSTRACT

Presented systems and methods facilitate efficient and effective generation and delivery of radiation. A radiation generation system can comprise: a particle beam gun, a high energy dissipation anode target (HEDAT); and a liquid anode control component. In some embodiments, the particle beam gun generates an electron beam. The HEDAT includes a solid anode portion (HEDAT-SAP) and a liquid anode portion (HEDAT-LAP) that are configured to receive the electron beam, absorb energy from the electron beam, generate a radiation beam, and dissipate heat. The radiation beam can include photons that can have radiation characteristics (e.g., X-ray wavelength, ionizing capability, etc.). The liquid anode control component can control a liquid anode flow to the HEDAT. The HEDAT-SAP and HEDAT-LAP can cooperatively operate in radiation generation and their configuration can be selected based upon contribution of respective HEDAT-SAP and the HEDAT-LAP characteristics to radiation generation.

20 Claims, 12 Drawing Sheets

(51) Int. Cl.
*A61N 5/10* (2006.01)
*H01J 35/18* (2006.01)

(52) U.S. Cl.
CPC . *H01J 2235/082* (2013.01); *H01J 2235/1204* (2013.01); *H01J 2235/127* (2013.01)

(56) References Cited

U.S. PATENT DOCUMENTS

| | | |
|---|---|---|
| 5,153,900 A | 10/1992 | Nomikos et al. |
| 5,267,294 A | 11/1993 | Kuroda |
| 5,550,378 A | 8/1996 | Skillicorn et al. |
| 5,610,967 A | 3/1997 | Moorman et al. |
| 5,625,663 A | 4/1997 | Swerdloff et al. |
| 5,682,412 A | 10/1997 | Skillicorn et al. |
| 5,757,885 A | 5/1998 | Yao et al. |
| 6,198,802 B1 | 3/2001 | Elliott et al. |
| 6,222,544 B1 | 4/2001 | Tarr et al. |
| 6,234,671 B1 | 5/2001 | Solomon et al. |
| 6,260,005 B1 | 7/2001 | Yang et al. |
| 6,379,380 B1 | 4/2002 | Satz |
| 6,411,675 B1 | 6/2002 | Llacer |
| 6,445,766 B1 | 9/2002 | Whitham |
| 6,504,899 B2 | 1/2003 | Pugachev et al. |
| 6,580,940 B2 | 6/2003 | Gutman |
| 6,993,112 B2 | 1/2006 | Hesse |
| 7,268,358 B2 | 9/2007 | Ma et al. |
| 7,453,983 B2 | 11/2008 | Schildkraut et al. |
| 7,515,681 B2 | 4/2009 | Ebstein |
| 7,522,706 B2 | 4/2009 | Lu et al. |
| 7,560,715 B2 | 7/2009 | Pedroni |
| 7,590,219 B2 | 9/2009 | Maurer, Jr. et al. |
| 7,616,735 B2 | 11/2009 | Maciunas et al. |
| 7,623,623 B2 | 11/2009 | Raanes et al. |
| 7,778,691 B2 | 8/2010 | Zhang et al. |
| 7,807,982 B2 | 10/2010 | Nishiuchi et al. |
| 7,831,289 B2 | 11/2010 | Riker et al. |
| 7,835,492 B1 | 11/2010 | Sahadevan |
| 7,907,699 B2 | 3/2011 | Long et al. |
| 8,284,898 B2 | 10/2012 | Ho et al. |
| 8,306,184 B2 | 11/2012 | Chang et al. |
| 8,401,148 B2 | 3/2013 | Lu et al. |
| 8,406,844 B2 | 3/2013 | Ruchala et al. |
| 8,559,596 B2 | 10/2013 | Thomson et al. |
| 8,600,003 B2 | 12/2013 | Zhou et al. |
| 8,613,694 B2 | 12/2013 | Walsh |
| 8,636,636 B2 | 1/2014 | Shukla et al. |
| 8,644,571 B1 | 2/2014 | Schulte et al. |
| 8,716,663 B2 | 5/2014 | Brusasco et al. |
| 8,836,332 B2 | 9/2014 | Shvartsman et al. |
| 8,847,179 B2 | 9/2014 | Fujitaka et al. |
| 8,903,471 B2 | 12/2014 | Heid |
| 8,917,813 B2 | 12/2014 | Maurer, Jr. |
| 8,948,341 B2 | 2/2015 | Beckman |
| 8,958,864 B2 | 2/2015 | Amies et al. |
| 8,983,573 B2 | 3/2015 | Carlone et al. |
| 8,986,186 B2 | 3/2015 | Zhang et al. |
| 8,992,404 B2 | 3/2015 | Graf et al. |
| 8,995,608 B2 | 3/2015 | Zhou et al. |
| 9,018,603 B2 | 4/2015 | Loo et al. |
| 9,033,859 B2 | 5/2015 | Fieres et al. |
| 9,079,027 B2 | 7/2015 | Agano et al. |
| 9,149,656 B2 | 10/2015 | Tanabe |
| 9,155,908 B2 | 10/2015 | Meltsner et al. |
| 9,233,260 B2 | 1/2016 | Slatkin et al. |
| 9,258,876 B2 | 2/2016 | Cheung et al. |
| 9,283,406 B2 | 3/2016 | Prieels |
| 9,308,391 B2 | 4/2016 | Liu et al. |
| 9,330,879 B2 | 5/2016 | Lewellen et al. |
| 9,333,374 B2 | 5/2016 | Iwata |
| 9,468,777 B2 | 10/2016 | Fallone et al. |
| 9,517,358 B2 | 12/2016 | Velthuis et al. |
| 9,526,918 B2 | 12/2016 | Kruip |
| 9,545,444 B2 | 1/2017 | Strober et al. |
| 9,583,302 B2 | 2/2017 | Figueroa Saavedra et al. |
| 9,636,381 B2 | 5/2017 | Basile |
| 9,636,525 B1 | 5/2017 | Sahadevan |
| 9,649,298 B2 | 5/2017 | Djonov et al. |
| 9,656,098 B2 | 5/2017 | Goer |
| 9,694,204 B2 | 7/2017 | Hardemark |
| 9,776,017 B2 | 10/2017 | Flynn et al. |
| 9,786,054 B2 | 10/2017 | Taguchi et al. |
| 9,786,093 B2 | 10/2017 | Svensson |
| 9,786,465 B2 | 10/2017 | Li et al. |
| 9,795,806 B2 | 10/2017 | Matsuzaki et al. |
| 9,801,594 B2 | 10/2017 | Boyd et al. |
| 9,844,358 B2 | 12/2017 | Wiggers et al. |
| 9,854,662 B2 | 12/2017 | Mishin |
| 9,884,206 B2 | 2/2018 | Schulte et al. |
| 9,931,522 B2 | 4/2018 | Bharadwaj et al. |
| 9,962,562 B2 | 5/2018 | Fahrig et al. |
| 9,974,977 B2 | 5/2018 | Lachaine et al. |
| 9,987,502 B1 | 6/2018 | Gattiker et al. |
| 10,007,961 B2 | 6/2018 | Grudzinski et al. |
| 10,022,564 B2 | 7/2018 | Thieme et al. |
| 10,071,264 B2 | 9/2018 | Liger |
| 10,080,912 B2 | 9/2018 | Kwak et al. |
| 10,092,774 B1 | 10/2018 | Vanderstraten et al. |
| 10,183,179 B1 | 1/2019 | Smith et al. |
| 10,188,875 B2 | 1/2019 | Kwak et al. |
| 10,206,871 B2 | 2/2019 | Lin et al. |
| 10,212,800 B2 | 2/2019 | Agustsson et al. |
| 10,232,193 B2 | 3/2019 | Iseki |
| 10,258,810 B2 | 4/2019 | Zwart et al. |
| 10,272,264 B2 | 4/2019 | Ollila et al. |
| 10,279,196 B2 | 5/2019 | West et al. |
| 10,293,184 B2 | 5/2019 | Pishdad et al. |
| 10,307,614 B2 | 6/2019 | Schnarr |
| 10,307,615 B2 | 6/2019 | Ollila et al. |
| 10,315,047 B2 | 6/2019 | Glimelius et al. |
| 10,413,755 B1 | 9/2019 | Sahadevan |
| 10,449,389 B2 | 10/2019 | Ollila et al. |
| 10,485,988 B2 | 11/2019 | Kuusela et al. |
| 10,525,285 B1 | 1/2020 | Friedman |
| 10,549,117 B2 | 2/2020 | Vanderstraten et al. |
| 10,603,514 B2 | 3/2020 | Grittani et al. |
| 10,609,806 B2 | 3/2020 | Roecken et al. |
| 10,636,609 B1 | 4/2020 | Bertsche et al. |
| 10,660,588 B2 | 5/2020 | Boyd et al. |
| 10,661,100 B2 | 5/2020 | Shen |
| 10,682,528 B2 | 6/2020 | Ansorge et al. |
| 10,702,716 B2 | 7/2020 | Heese |
| 10,758,746 B2 | 9/2020 | Kwak et al. |
| 10,870,018 B2 | 12/2020 | Bartkoski et al. |
| 2007/0287878 A1 | 12/2007 | Fantini et al. |
| 2010/0178245 A1 | 7/2010 | Arnsdorf et al. |
| 2010/0260317 A1 | 10/2010 | Chang et al. |
| 2011/0006224 A1 | 1/2011 | Maltz et al. |
| 2011/0091015 A1 | 4/2011 | Yu et al. |
| 2012/0157746 A1 | 6/2012 | Meltsner et al. |
| 2012/0171745 A1 | 7/2012 | Itoh |
| 2013/0231516 A1 | 9/2013 | Loo et al. |
| 2014/0177807 A1 | 6/2014 | Lewellen et al. |
| 2014/0185776 A1 | 7/2014 | Li et al. |
| 2014/0275706 A1 | 9/2014 | Dean et al. |
| 2014/0369476 A1* | 12/2014 | Harding ............... H01J 35/186 378/140 |
| 2015/0011817 A1 | 1/2015 | Feng |
| 2015/0202464 A1 | 7/2015 | Brand et al. |
| 2015/0306423 A1 | 10/2015 | Bharat et al. |
| 2016/0279444 A1 | 9/2016 | Schlosser |
| 2016/0310764 A1 | 10/2016 | Bharadwaj et al. |
| 2017/0189721 A1 | 7/2017 | Sumanaweera et al. |
| 2017/0203129 A1 | 7/2017 | Dessy |
| 2017/0281973 A1 | 10/2017 | Allen et al. |
| 2018/0021594 A1 | 1/2018 | Papp et al. |
| 2018/0043183 A1 | 2/2018 | Sheng et al. |
| 2018/0056090 A1 | 3/2018 | Jordan et al. |
| 2018/0099154 A1 | 4/2018 | Prieels |
| 2018/0099155 A1 | 4/2018 | Prieels et al. |
| 2018/0099159 A1 | 4/2018 | Forton et al. |
| 2018/0154183 A1 | 6/2018 | Sahadevan |
| 2018/0197303 A1 | 7/2018 | Jordan et al. |
| 2018/0236268 A1 | 8/2018 | Zwart et al. |
| 2019/0022407 A1 | 1/2019 | Abel et al. |

(56) References Cited

U.S. PATENT DOCUMENTS

| | | |
|---|---|---|
| 2019/0022422 A1 | 1/2019 | Trail et al. |
| 2019/0054315 A1 | 2/2019 | Isola et al. |
| 2019/0070435 A1 | 3/2019 | Joe Anto et al. |
| 2019/0168027 A1 | 6/2019 | Smith et al. |
| 2019/0255361 A1 | 8/2019 | Mansfield |
| 2019/0299027 A1 | 10/2019 | Fujii et al. |
| 2019/0299029 A1 | 10/2019 | Inoue |
| 2019/0351259 A1 | 11/2019 | Lee et al. |
| 2020/0001118 A1 | 1/2020 | Snider, III et al. |
| 2020/0022248 A1 | 1/2020 | Yi et al. |
| 2020/0030633 A1 | 1/2020 | Van Heteren et al. |
| 2020/0035438 A1 | 1/2020 | Star-Lack et al. |
| 2020/0069818 A1 | 3/2020 | Jaskula-Ranga et al. |
| 2020/0164224 A1 | 5/2020 | Vanderstraten et al. |
| 2020/0178890 A1 | 6/2020 | Otto |
| 2020/0197730 A1 | 6/2020 | Safavi-Naeini et al. |
| 2020/0254279 A1 | 8/2020 | Ohishi |
| 2020/0269068 A1 | 8/2020 | Abel et al. |
| 2020/0276456 A1 | 9/2020 | Swerdloff |
| 2020/0282234 A1 | 9/2020 | Folkerts et al. |

FOREIGN PATENT DOCUMENTS

| | | |
|---|---|---|
| CN | 107362464 | 11/2017 |
| CN | 109966662 | 7/2019 |
| CN | 111481840 | 8/2020 |
| CN | 111481841 | 8/2020 |
| EA | 010207 | 6/2008 |
| EP | 0979656 | 2/2000 |
| EP | 3338858 | 6/2018 |
| EP | 3384961 | 10/2018 |
| EP | 3421087 | 1/2019 |
| EP | 3453427 | 3/2019 |
| EP | 3586920 | 1/2020 |
| JP | 2617283 | 6/1997 |
| JP | 2019097969 | 6/2019 |
| WO | 2007017177 | 2/2007 |
| WO | 2010018476 | 2/2010 |
| WO | 2013081218 | 6/2013 |
| WO | 2013133936 | 9/2013 |
| WO | 2014139493 | 9/2014 |
| WO | 2015038832 | 3/2015 |
| WO | 2015102680 | 7/2015 |
| WO | 2016122957 | 8/2016 |
| WO | 2017156316 | 9/2017 |
| WO | 2017174643 | 10/2017 |
| WO | 2018137772 | 8/2018 |
| WO | 2018152302 | 8/2018 |
| WO | 2019097250 | 5/2019 |
| WO | 2019103983 | 5/2019 |
| WO | 2019164835 | 8/2019 |
| WO | 2019166702 | 9/2019 |
| WO | 2019185378 | 10/2019 |
| WO | 2019222436 | 11/2019 |
| WO | 2020018904 | 1/2020 |
| WO | 2020064832 | 4/2020 |
| WO | 2020107121 | 6/2020 |
| WO | 2020159360 | 8/2020 |

OTHER PUBLICATIONS

Ibrahim Oraiqat et al., "An Ionizing Radiation Acoustic Imaging (iRAI) Technique for Real-Time Dosimetric Measurements for FLASH Radiotherapy," Medical Physics, vol. 47, Issue10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5lbHNldmllci5jb20vY29udGVudC9hcnRpY2xlL3BpaS9zMDE2Nz gxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/ doi: 10.1118/1.4761951.

Favaudon et al., "Ultrahigh dose-rate, "flash" irradiation minimizes the side-effects of radiotherapy," Cancer / Radiotherapy, vol. 19, Issues 6-7, Oct. 2015, pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.

Bjorn Zackrisson, "Biological Effects Of High Energy Radiation And Ultra High Dose Rates," Umea University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, p. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated adiation therapy," Int. J. Radiation Oncology Biol. Phys., vol. 51, Issue 5, p. 1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

A. J. Lomax et al., "Intensity modulated proton therapy: A clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomotherapy in Nasopharynx Cancer: Planning Comparison and NTCP Evaluation," Int. J. Radiation Oncology

(56) References Cited

OTHER PUBLICATIONS

Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for early and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng-pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fedrik_light.pdf.

Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego—Admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.

J. Groen, "FLASH optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019. https://www.ncbi.nlm.nih.gov/pmc/articles/PMC5904040/ Published in final edited form as: Med Phys. Apr. 2018; 45(4): 1338-1350. Published online Mar. 1, 2018. doi: 10 1002/mp.12788 Accepted manuscript online: Feb. 2, 2018.

Paul Morel et al., "Spot weight adaptation for moving target in spot scanning proton therapy," Frontiers in Oneology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by Real-Time Imaging and Gating and Reduces Equipment Size," PLoS ONE, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "FLASH radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.

Mevion Medical Systems, "Focus On The Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp.

(56) References Cited

OTHER PUBLICATIONS 587-593, Radiation Research Society, Published: Aug. 27, 2020, doi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle adiotherapy using clinical proton, helium-, carbon- and oxygen ion beams," Oncotarget, Aug. 30, 2016, vol. 7, No. 35, p. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of FLASH Ultra-High Dose-Rate Studies or Proton and Heavy Ion Radiotherapy," Radiat Res. Author manuscript; available in PMC Jan. 1, 2021. https://www.ncbi.nlm.nih.gov/pmc/articles/PMC6949397/ Published in final edited form as: Radiat Res. Jan. 2020; 193(1): 1-4. Published online Oct. 28, 2019. doi: 10.1667/RR15537.1.

Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

"FlashRad: Ultra-high dose-rate FLASH radiotherapy to minimize the complications of radiotherapy," 2014, https://siric.curie.fr/sites/default/files/atoms/files/flashrad.pdf.

Tami Freeman, "Flash radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

IntraOp Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A FLASH back to radiotherapy's past and then fast forward to the future," J Cancer Prev Curr Res. 2019;10(6):142-144. published Nov. 13, 2019, DOI: 10.15406/jcpcr.2019.10.00407.

P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: FLASH: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp.13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/ Published in final edited form as: Radiother Oncol. Oct. 2019; 139: 51-55. Published online Mar. 5, 2019. doi: 10.1016/j.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement, S164-S165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394/.

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.

OncoLink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for-me.

Marco Durante et al., "Faster and safer? FLASH ultra-high dose rate in radiotherapy," Br J Radiol 2018; 91(1082):Jun. 28, 2017, British Institute of Radiology, Published Online: Dec. 15, 2017, https://doi.org/10.1259/bjr.20170628.

John R. Fischer, "PMB launches FLASH radiotherapy system for use in clinical trials," Healthcare Business News, Jun. 29, 2020, DOTmed.com, Inc., https://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432.CCR-17-3375.full.pdf.

* cited by examiner

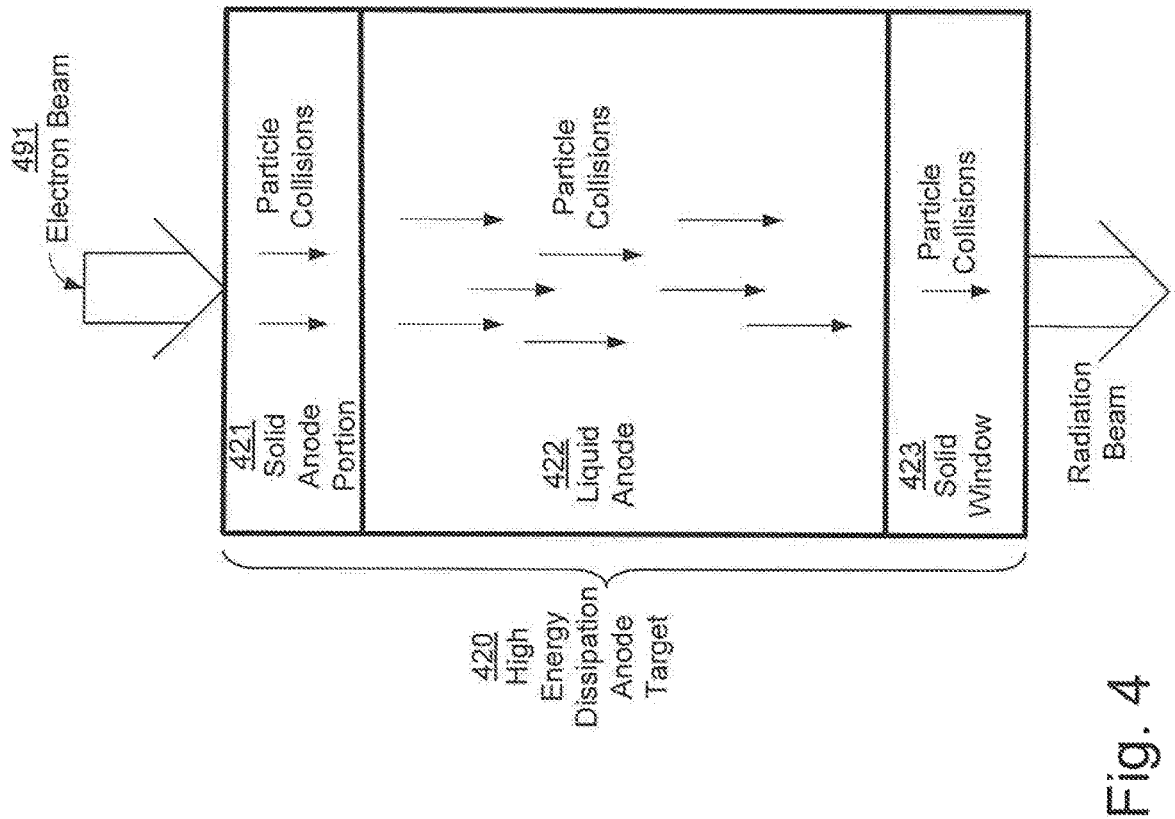
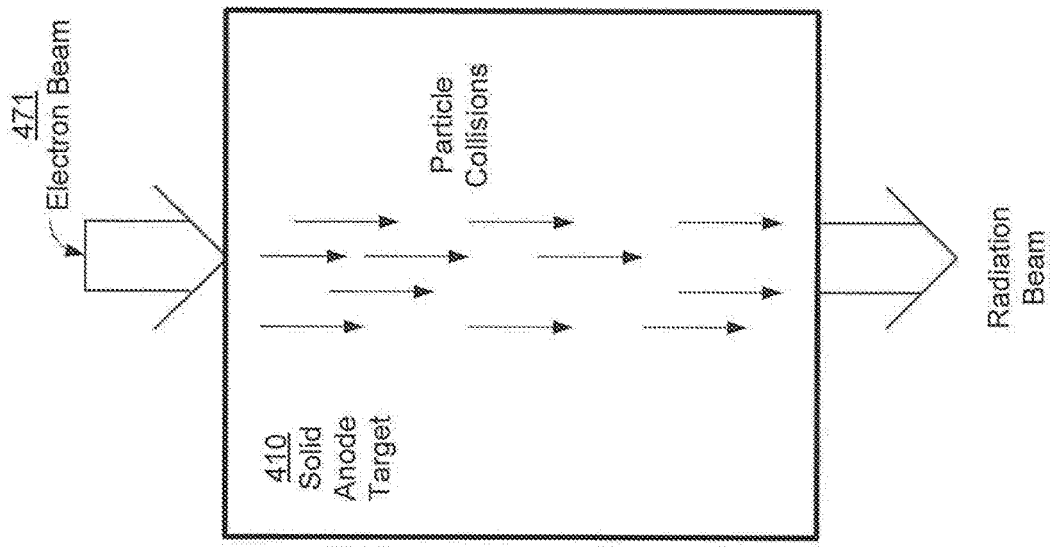
Fig. 4

| Alloy | Melting point | Eutectic? | Bismuth | Lead | Tin | Indium | Cadmium | Thallium | Gallium | Antimony |
|---|---|---|---|---|---|---|---|---|---|---|
| Rose's metal | 98 °C (208 °F) | no | 50% | 25% | 25% | - | - | - | - | - |
| Cerrosafe | 74 °C (165 °F) | no | 42.5% | 37.7% | 11.3% | - | 8.5% | - | - | - |
| Wood's metal | 70 °C (158 °F) | yes | 50% | 26.7% | 13.3% | - | 10% | - | - | - |
| Field's metal | 62 °C (144 °F) | yes | 32.5% | - | 16.5% | 51% | - | - | - | - |
| Cerrolow 136 | 58 °C (136 °F) | yes | 49% | 18% | 12% | 21% | - | - | - | - |
| Cerrolow 117 | 47.2 °C (117 °F) | yes | 44.7% | 22.6% | 8.3% | 19.1% | 5.3% | - | - | - |
| Bi-Pb-Sn-Cd-In-Tl | 41.5 °C (107 °F) | yes | 40.3% | 22.2% | 10.7% | 17.7% | 8.1% | 1.1% | - | - |
| Galinstan | −19 °C (−2 °F) | yes | <1.5% | - | 9.5-10.5% | 21-22% | - | - | 68.5-69.5% | <1.5% |

Fig. 7

| 871 Solid Anode Portion (Channel Wall) | 821 Liquid Anode Portion Channel | 872 Channel Wall | 822 Liquid Anode Portion Channel | 873 Channel Wall (Solid Anode Portion) | 823 Liquid Anode Portion Channel | 874 Channel Wall | 824 Liquid Anode Portion Channel | 875 Solid Anode Portion (Channel Wall) |

878 Channel Wall
877 Channel Wall

1210
Receiving an electron beam at a high energy anode target.

1220
Generating radiation by collisions of the electron beam particles in with components of the high energy dissipation anode target (HEDAT).

1230
Dissipating heat resulting from energy absorption in the HEDAT.

1240
Controlling a flow of liquid anode material to and from the a liquid anode portion of the high energy dissipation target.

Fig. 12

RADIATION ANODE TARGET SYSTEMS AND METHODS

RELATED APPLICATIONS

This application is a continuation claiming the benefit of and priority to application Ser. No. 16/045,598 entitled "Radiation Anode Target Systems and Methods", filed on Jul. 25, 2018, which is incorporated herein by reference.

FIELD OF THE INVENTION

The present invention relates to the field of radiation beam generation and control. In one embodiment, systems and methods facilitate fast and effective application of radiation therapy.

BACKGROUND

Radiation beams can be utilized in a number of different applications and accurately applying an appropriate amount of radiation can be very important. Radiation beam therapy typically includes directing a radiation beam at an area of tissue. There can be various different types of radiation beams (e.g., photon, ionizing particle, etc.). The radiation beams are typically used to stop the growth or spread of the targeted tissue cells by killing them or degrading their cell division ability. While radiation therapy is generally considered beneficial, there can be a number of potential side effects. The side effects can include unintended damage to DNA of healthy tissue cells. The effectiveness of radiation therapy is primarily a function of the dose or amount of ionizing radiation that is applied to cancerous cells while avoiding impacts to healthy cells.

The amount of radiation that is applied to the tissue is typically a function of a dose rate and time the targeted tissue is exposed to the radiation. In some implementations, the dose rate corresponds to the "current" of charged particles used to generate the radiation. The charged particle (e.g., proton, electron, etc.) can be directed at the tissue or can be directed at an intermediate target that produces another fundamental or elementary particle (e.g., photons, neutrons, etc,) which are directed at the tissue. The elementary particles can have radiation characteristics (e.g., X-ray wavelength, ionizing capabilities, etc.). Higher dose rates usually enable shorter exposure times and that can have a number of benefits, including less opportunity for extraneous events to influence the therapy, increased productivity, and greater convenience to the patient. Some conventional approaches have attempted to increase dose rate through higher MeV values. However, developing systems and methods compatible with higher MeV values can be difficult and problematic for conventional anode approaches. For example, use of higher MeV values can produce excess neutrons, which results in increased costs associated with measures (e.g., increased shielding, etc.) to counteract affects of the excess neutrons.

One considerable conventional obstacle is maintaining performance (e.g., radiation output levels, component structural integrity, etc.) while avoiding problematic conditions (e.g., overheating, environmental impacts, etc.). Heat loading capabilities of traditional solid anode targets (e.g., used in incident electron beam deceleration, used in production of Brehmmstralung radiation, etc.) do not typically provide adequate heat dissipation at high energy densities (e.g., power into the target) and the targets begin to melt and lose performance characteristics. Conventional improvements to a solid anode target (e.g., a rotating solid anode target, etc.) are usually difficult to employ as transmission targets and do not typically offer much improvement in heat dissipation. Traditional approaches using free flowing liquid anode jet streams can result in reduced and inconsistent radiation generation.

SUMMARY

Presented systems and methods facilitate efficient and effective generation and delivery of radiation. In some embodiments, a radiation generation system comprises: a particle beam gun, a high energy dissipation anode target (HEDAT); and a liquid anode control component. The radiation system can be a therapeutic radiation system. In one exemplary embodiment, the particle beam gun generates an electron beam. The HEDAT includes a solid anode portion (HEDAT-SAP) and a liquid anode portion (HEDAT-LAP) configured to receive the electron beam, absorb energy from the electron beam, generate a radiation beam, and dissipate heat. The radiation beam can include photons that can have radiation characteristics (e.g., X-ray wavelength, ionizing capabilities, etc.). The liquid anode control component is configured to control a flow of a liquid anode to the HEDAT.

The HEDAT-SAP and HEDAT-LAP cooperatively operate in radiation generation and control. The configuration of the HEDAT-SAP and the HEDAT-LAP can be selected based upon contributions of respective HEDAT-SAP and HEDAT-LAP characteristics to radiation generation and heat dissipation. The received electron beam can have an energy characteristic equal to or greater than 1 MeV. The HEDAT includes solid surfaces that confine the flow of the liquid anode through the HEDAT. A surface that confines the flow of the liquid anode through the HEDAT can also be a surface of the solid anode target. The liquid anode control component can control pressure and temperature of the liquid anode. The liquid anode can absorb heat from electron beam collisions within the liquid anode and heat via conduction from the solid energy anode. In some embodiments, the HEDAT can include a surface that forms a wall of a channel configured to confine a flow of a liquid anode. The HEDAT-SAP can be made from a material that has at least one of the following characteristics: low density, low atomic number, high heat capacity, high thermal conductivity, high melting point, high Yield strength at high temperatures, high electrical conductivity, Rad hard, resistant to corrosive characteristics of the HEDAT-LAP, and so on. The HEDAT-SAP and HEDAT-LAP cooperatively operate to enhance energy compatibility characteristics of the HEDAT. The liquid anode can include a material that has at least one of the following characteristics: high heat capacity, low melting point, high thermal conductivity, high boiling point, high density, high atomic number, low viscosity, non-corrosive, and so on.

In some embodiments, a radiation method comprises: receiving an electron beam at a high energy dissipation anode target (HEDAT); generating radiation in a solid anode portion (HEDAT-SAP) and a liquid anode portion (HEDAT-LAP) of the HEDAT; dissipating heat; and controlling a flow of liquid anode material to and from the HEDAT-LAP. The radiation generation can include absorbing energy resulting from electron beam collisions in the HEDAT-SAP and the HEDAT-LAP. The heat resulting from energy absorption in the solid anode target and a liquid anode target is dissipated. In one embodiment, the HEDAT-LAP dissipates heat generated internally by particle collisions within the HEDAT- LAP and also heat resulting from conduction transfer from the HEDAT-SAP. Dissipating the heat includes flowing cool liquid anode material into the HEDAT and warm liquid anode material out of the HEDAT (e.g., the liquid anode leaving the HEDAT is warmer than the liquid anode entering the HEDAT). The radiation method can also include forwarding a resulting generated radiation beam to a treatment target.

In some embodiments, a radiation therapy system comprises: a beam generation system that generates and transports a radiation beam in accordance with a prescribed treatment plan, and a control component that receives information on radiation delivery associated with the radiation beam and directs execution of a prescribed treatment plan. The radiation beam can include elementary particles that have radiation characteristics. In some embodiments, a beam generation system comprises: a particle beam gun, a high energy dissipation anode target (HEDAT); and a liquid anode control component. The beam generation system can include a linear accelerator and components that direct an elementary particle beam in a direction toward and into a target. The target may be mounted on or be a part of a fixed, rotating, or movable gantry so that it can be moved relative to a supporting device that supports the patient.

BRIEF DESCRIPTION OF THE DRAWINGS

The accompanying drawings together with the description are incorporated in and form a part of this specification. They illustrate exemplary embodiments and explain exemplary principles of the disclosure. They are not intended to limit the present invention to the particular embodiments illustrated therein. The drawings are not to scale unless otherwise specifically indicated

FIG. 4 is a block diagram comparison of radiation emitting collisions in an exemplary HEDAT and conventional solid anode target in accordance with one embodiment.

FIG. 7 is a table of liquid anode elements in accordance with one embodiment.

FIG. 9 is a block diagram of an exemplary different side view of a HEDAT in accordance with one embodiment.

FIG. 12 is a block diagram of an exemplary particle beam generation method in accordance with one embodiment.

DETAILED DESCRIPTION OF THE INVENTION

Reference will now be made in detail to the illustrated, exemplary embodiments in the accompanying drawings. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one ordinarily skilled in the art that the present invention may be practiced without these specific details. In other instances, well known methods, procedures, components, and circuits have not been described in detail as not to unnecessarily obscure aspects of the current invention.

Presented systems and methods facilitate efficient and effective radiation generation and control. In one embodiment, a high energy dissipation target is capable of operating with high energy beams. The high energy dissipation target can operate as an anode to produce radiation. In one exemplary implementation, a high energy dissipation anode target (HEDAT) includes a solid anode portion (HEDAT-SAP) and a liquid anode portion (HEDAT-LAP). The HEDAT-SAP and HEDAT-LAP can be configured to collaboratively contribute to radiation emission, energy absorption, heat dissipation, and so on. A HEDAT-LAP can enable utilization of a HEDAT-SAP with certain configuration characteristics (e.g., heat dissipation characteristic, radiation generation characteristics, etc.), and vice versa. The HEDAT-SAP and HEDAT-LAP cooperatively operate to enhance energy compatibility characteristics of the HEDAT. In one embodiment, a HEDAT is capable of receiving a high energy input (e.g., greater than 1 MeV) and efficiently generating radiation while maintaining system integrity (e.g., providing accurate radiation output, enabling output fidelity, avoiding overheating, etc.).

Figure 1:
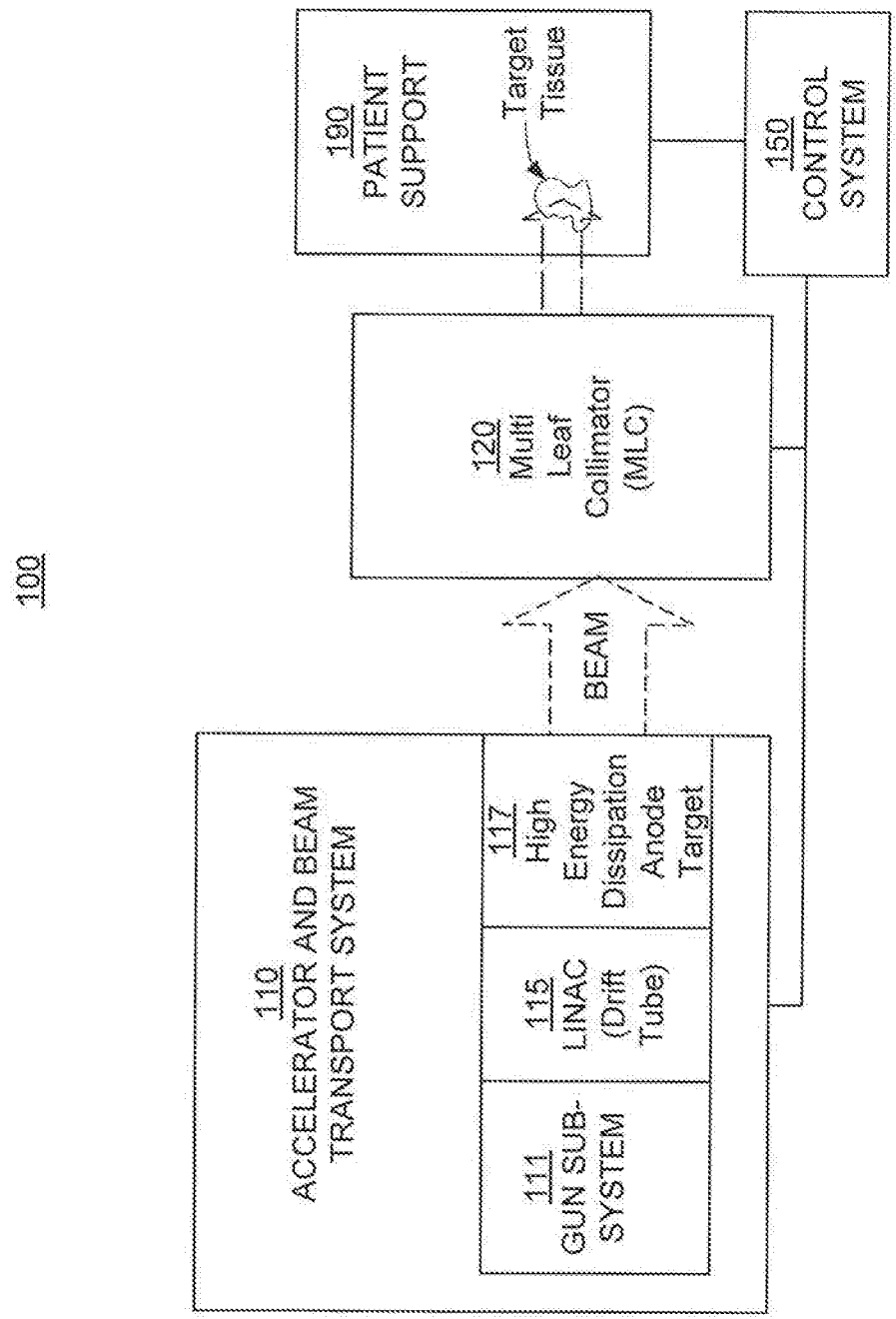
FIG. 1 is a block diagram of an exemplary radiation system in accordance with one embodiment.

FIG. 1 is a block diagram of an exemplary radiation therapy system 100. Radiation therapy system 100 includes an accelerator and beam transport system 110, multi-leaf collimator (MLC) 120, control system 150, and supporting device 190. In one exemplary implementation, the accelerator and beam transport system 110 generates and transports a radiation beam of elementary particles (e.g., photons, etc.) that have radiation characteristics. In one embodiment, a plurality of elementary particles travel in substantially the same direction and are included in a beam. The beam of elementary particles can form a radiation beam. In one exemplary implementation, the radiation beam includes X-rays.

Accelerator and beam transport system 110 includes gun subsystem 111, drift tube 115, and high energy dissipation anode target (HEDAT) 117. Gun subsystem 111 generates a particle beam (e.g., electron beam, etc.). In one embodiment, gun subsystem 111 is compatible with timing control of beam generation operations in a microwave frequency range. Accelerator and beam transport system 110 can include a particle accelerator that accelerates a particle generated by the gun subsystem 111.

The system is compatible with a variety of accelerators (e.g., a continuous wave beam accelerator, betatron, an isochronous cyclotron, a pulsed accelerator, a synchrocyclotron, a synchrotron, etc.). In one embodiment, accelerator and beam transport system 110 includes a linear accelerator (LINAC). In one exemplary implementation, the accelerator is capable of relatively continuous wave output and extracts particles with a specified energy. The LINAC drift tube 115 allows electrons emitted by the gun-subsystem 111 to travel to the HEDAT 117. In one embodiment, the electrons are decelerated by a HEDAT used in production of Brehmmstralung radiation at high energies (e.g., 1-25 MeV, etc.).

In one embodiment, the gun subsystem 111 generates a primary electron particle beam that is used to create a secondary photon radiation beam. A primary electron particle beam generator may be configured to correlate the time of secondary photon emission with the primary electron particle beam generation (e.g., to further improve signal-to-noise ratio, etc.). HEDAT 117 can receive high energy input (e.g., greater then 1 MeV, etc.) and generate relatively high quantity radiation while maintaining system integrity, including dissipating excess heat. In one exemplary implementation, the HEDAT generates radiation in the form of X-rays. Additional description of high energy anodes is presented in later portions of this specification.

The accelerator and beam transport system 110 can include various other components (e.g., dipole magnets, bending magnets, etc.) that direct (e.g., bend, steer, guide, etc.) a beam through the system in a direction toward and into the MLC 120. The accelerator and beam transport system 110 may also include components that are used to adjust the beam energy entering the MLC 120.

In one embodiment, MLC 120 includes components that control a beam shape. In one exemplary implementation, a MLC leaf can be independently adjusted (e.g., moved back-and-forth, etc.) to dynamically shape an aperture through which a beam can pass. The adjustments can be directed by control system 150. The aperture can block or not block portions of the beam and thereby control beam shape and exposure time. The beam can be considered a relatively well-defined beam. The MLC 120 can be used to aim the beam toward various locations within an object (e.g., a patient, target tissue, etc.). In one embodiment, the MLC 120 controls a radiation beam in "X and Y directions" to scan a target tissue volume.

The object (e.g., a target tissue volume in a patient, etc.) can be located on the supporting device 190 (e.g., a chair, couch, bench, table, etc.) in a treatment room. In one embodiment, the supporting device is moveable. The MLC 120 may be mounted on or a part of a fixed, rotating or movable gantry (not shown) so that it can be moved relative to the supporting device 190. The accelerator and beam transport system 110 can also be mounted on or be a part of the gantry. In another embodiment, the beam generation system is separate from the gantry. In one exemplary implementation, a separate beam generation system is in communication with the gantry.

In one embodiment, control system 150 receives and directs execution of a prescribed treatment plan. In one exemplary implementation, the control system 150 includes a computer system having a processor, memory, and user interface components (e.g. a keyboard, a mouse, a display, etc.). The control system 150 can control parameters and operations of the accelerator and beam transport system 110, MLC 120, and supporting device 190, including parameters such as the energy, intensity, direction, size, and shape of the beam. The control system 150 can receive data regarding operation of the system 100 and control the components according to data it receives. The data can be included in the prescribed treatment plan. In one embodiment, the control system 150 receives information and analyzes the performance and treatment being provided by radiation therapy system 100. In one embodiment, the control system 150 can direct adjustments to the radiation therapy system 100 based upon the analysis of dose and dose rate.

It is appreciated that a high energy dissipation anode target (HEDAT) can be compatible with a variety of radiation treatment approaches. A HEDAT can be utilized for high dose rate treatments. In one embodiment, a HEDAT is used to deliver radiation therapy capable of dose rates that correspond to time intervals of frozen movement or no movement in a treatment target. In one exemplary implementation, a radiation treatment dose rate is compatible with delivery of radiation to a treatment target in a chest area in a time interval corresponding to no movement in the chest area due to inhaling or exhaling a breath (e.g. no movement due to a lung expanding, contracting, etc.).

Some treatment or therapy approaches include ultra-high dose rate treatment or modality referred to as FLASH radiotherapy. Therapeutic windows associated with FLASH therapy often enable reduced normal tissue toxicity while maintaining cancerous tissue tumor control. In one embodiment, a HEDAT is used to deliver FLASH radiation therapy. In one exemplary implementation, the FLASH radiotherapy dose rate can be at least 4 Gray (Gy) in less than one second and as much as 20 Gy or 40 Gy in less than a second. The FLASH radiotherapy dose rate can be more than 40 Gy in less than one second. The radiation therapy systems and methods can also be compatible with multiple field treatment approaches in which different fields are associated with a particular treatment trajectory and a dose per field that is a portion or fraction of a total dose delivery.

Figure 2:
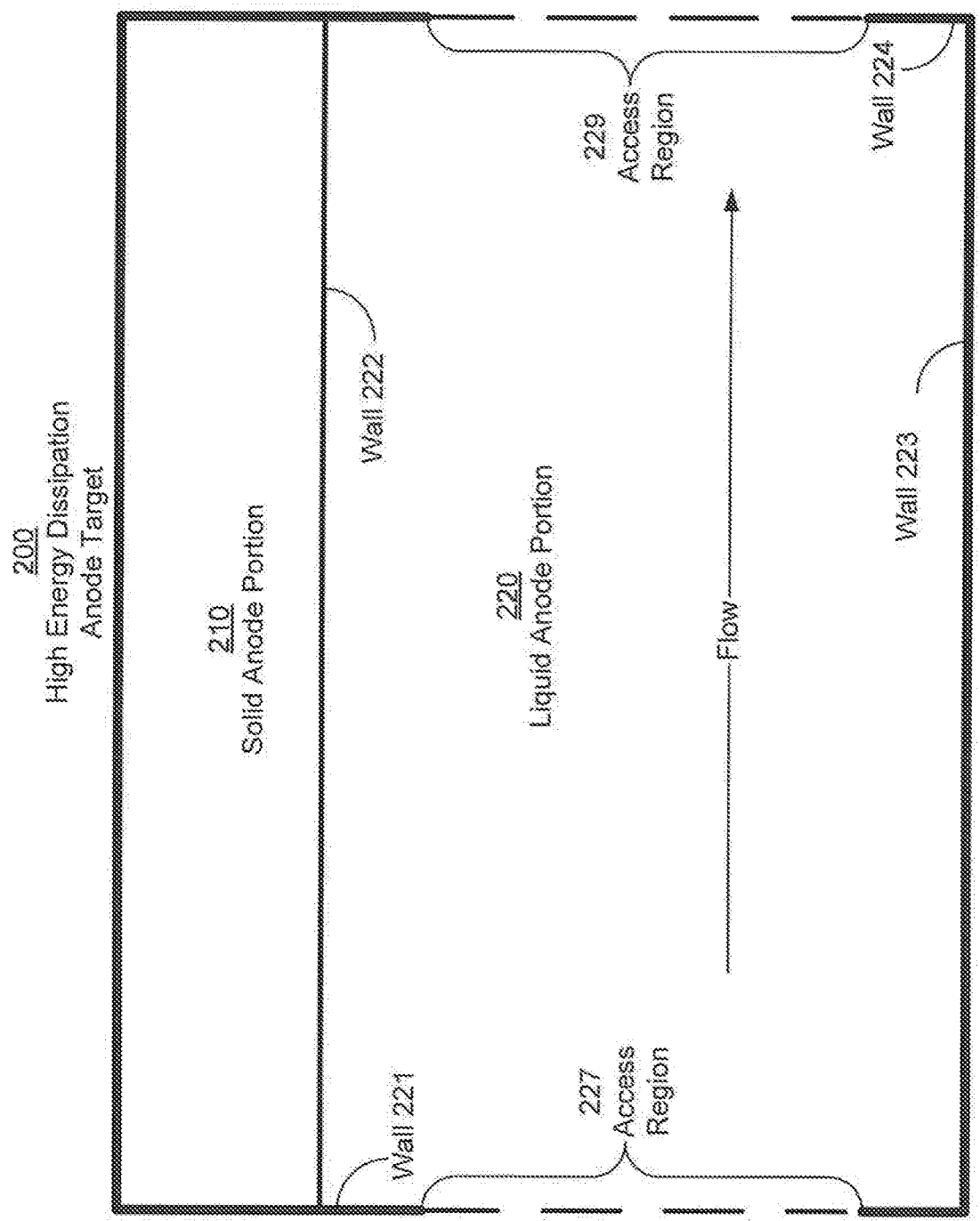
FIG. 2 is a block diagram of an exemplary HEDAT in accordance with one embodiment.

FIG. 2 is a block diagram of an exemplary HEDAT 200 in accordance with one embodiment. HEDAT 200 includes solid anode portion (HEDAT-SAP) 210 and liquid anode portion (HEDAT-LAP) 220. HEDAT-LAP 220 includes walls 221, 222, 223, and 224. Walls 221 and 224 include access regions 227 and 229. A liquid anode can flow through access regions 227 and 229. It is appreciated that other walls or surfaces of a HEDAT-LAP can also include access regions. In one exemplary implementation, the walls 221, 222, 223, and 224 can form a channel to contain and control the flow the liquid anode. A HEDAT-SAP can form a wall of a HEDAP-LAP. In one embodiment, HEDAT-SAP 210 can serve as wall 222 of HEDAT-LAP 220. The HEDAT-SAP 210 and HEDAT-LAP 220 cooperatively operate in radiation generation to augment or increase the compatibility characteristics of the HEDAT with high energy input. The HEDAT-SAP 220 and HEDAT-LAP 210 can be configured to collaboratively contribute to radiation emission, energy absorption, heat dissipation, and so on.

Figure 3:
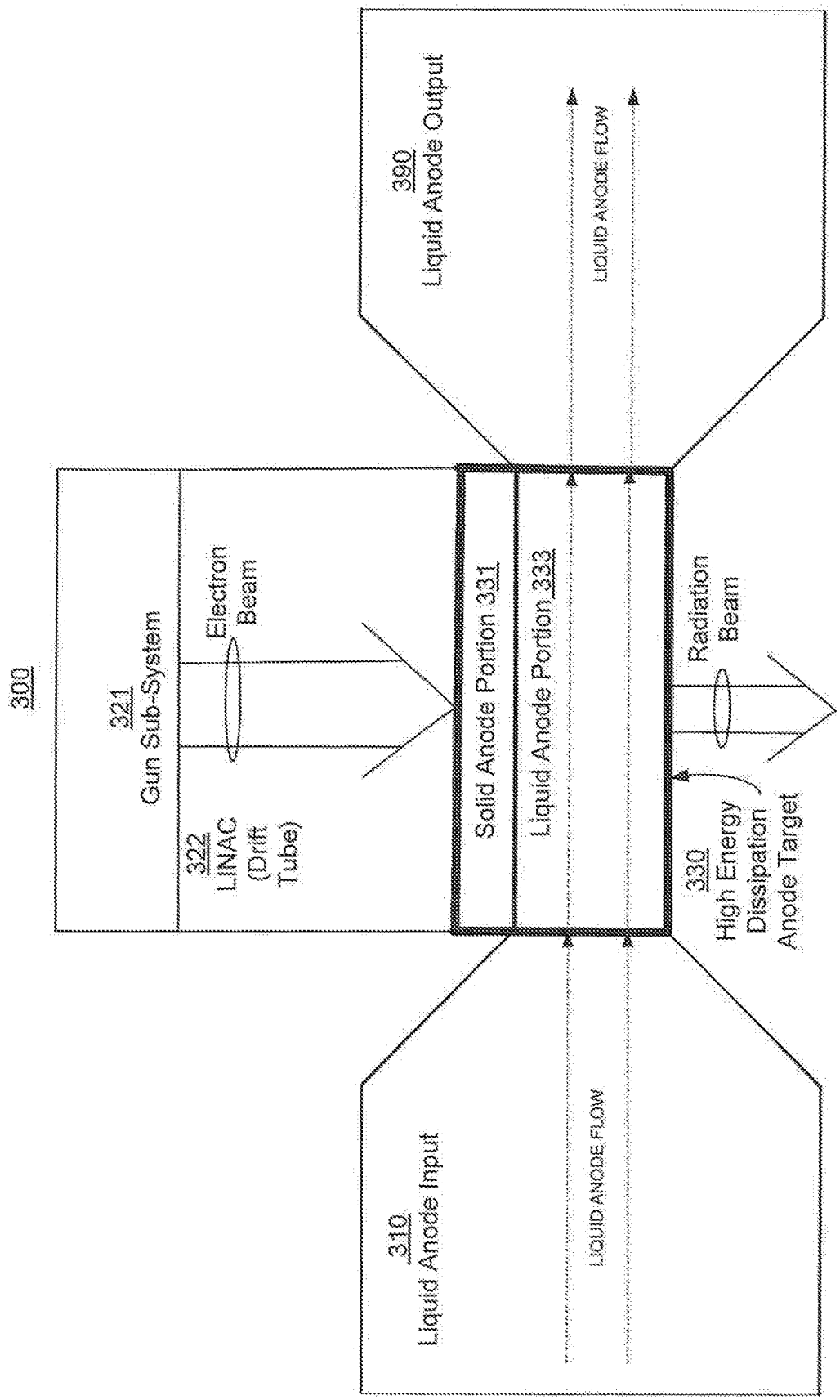
FIG. 3 is a block diagram of an exemplary HEDAT and system components in accordance with one embodiment.

FIG. 3 is a block diagram of an exemplary high energy radiation generation system 300. High energy radiation generation system 300 includes gun sub-system 321, LINAC drift tube 322, and HEDAT 330. In one embodiment, gun sub-system 321, LINAC drift tube 322, and HEDAT 330 are similar to gun subsystem 111, LINAC drift tube 115, and high energy anode 117. In one exemplary implementation, gun subsystem 321 generates an electron beam that is conveyed through LINAC drift tube 322 to HEDAT 330. HEDAT 330 includes HEDAT-SAP 331 and HEDAT-LAP 333. As the electrons from the electron beam travel through the HEDAT 330 there are collisions with components of the HEDAT-SAP 331 and HEDAT-LAP 333 and the collisions result in generation or emission of radiation. The radiation can include elementary particles. The radiation can include photons. The emissions can be configured in a radiation beam. The emissions can include X-rays. In some embodiments, a liquid anode flows from the liquid anode input 310 into the HEDAT-LAP 333 and out to the liquid anode output 390. The HEDAT 330 can facilitate utilization of a high energy input electron beam (e.g., greater than 1 MeV, etc).

In some embodiments, generation of the radiation beam is the result of electron collisions with elementary particles in both the HEDAT-SAP and the HEDAT-LAP, unlike a typical conventional system configured with just one type of anode material. The liquid anode portion contribution to both radiation generation and heat dissipation can enable utilization of higher energy input than a typical traditional approach that relies entirely on a solid anode. FIG. 4 is a block diagram comparison of an exemplary conventional solid anode target 410 and an exemplary HEDAT 420 in accordance with an exemplary embodiment. In a conventional solid anode target 410 all or most of the collisions and resulting heat generation occur within the solid anode target 410. The solid anode target 410 has relatively little heat dissipation capability (e.g., is basically limited to non-ionizing thermal radiation through the external surface and/or conduction etc.). The bulk of the heat is trapped within the solid anode target 410. The longer the electron beam 471 is applied, the greater the heat build up, eventually reaching a collapse or melting point.

In exemplary HEDAT 420, the collisions occur in both the HEDAT-SAP 421 and HEDAT-LAP 422. In one exemplary implementation, the bulk of the collisions happen in a liquid anode within the HEDAT-LAP 422. Even though the electron beam 491 may be applied to the HEDAT 420 for a relatively long period of time, movement of the liquid anode flow ensures a given portion of the liquid anode flow is not subjected or exposed to the electron beam for a full period of time the electron beam 491 is applied to the HEDAT 420. Thus, the heat does not continue to build up in a single given portion of the liquid anode the whole time the electron beam 491 is applied. In some embodiments, the solid window 423 also comprises a material that emits radiation and heat. In one exemplary implementation, the solid window 423 is also considered a HEDAT solid anode portion or HEDAT-SAP of HEDAT 420. In one exemplary embodiment, solid window 423 permits radiation from the HEDAT-SAP 421 and HEDAT-LAP 422 to pass or flow through and emit from the solid window 423 with negligible or little radiation generated in the solid window 423. The solid window 423 is can be considered a non-anode portion of the HEDAT 420.

The HEDAT-SAP 421, solid window 423, and HEDAT-LAP 422 are configured so that heat generation and dissipation avoid the melting or collapse point in HEDAT-SAP 421 and solid window 423. It is appreciated that a number of factors and characteristics can be included in the configuration selection of HEDAT-SAP 421, solid window 423, and HEDAT-LAP 422. In some embodiments, the HEDAT-SAP is thinner than a conventional approach solid portion that relies entirely on a solid anode for radiation generation.

Figure 5:
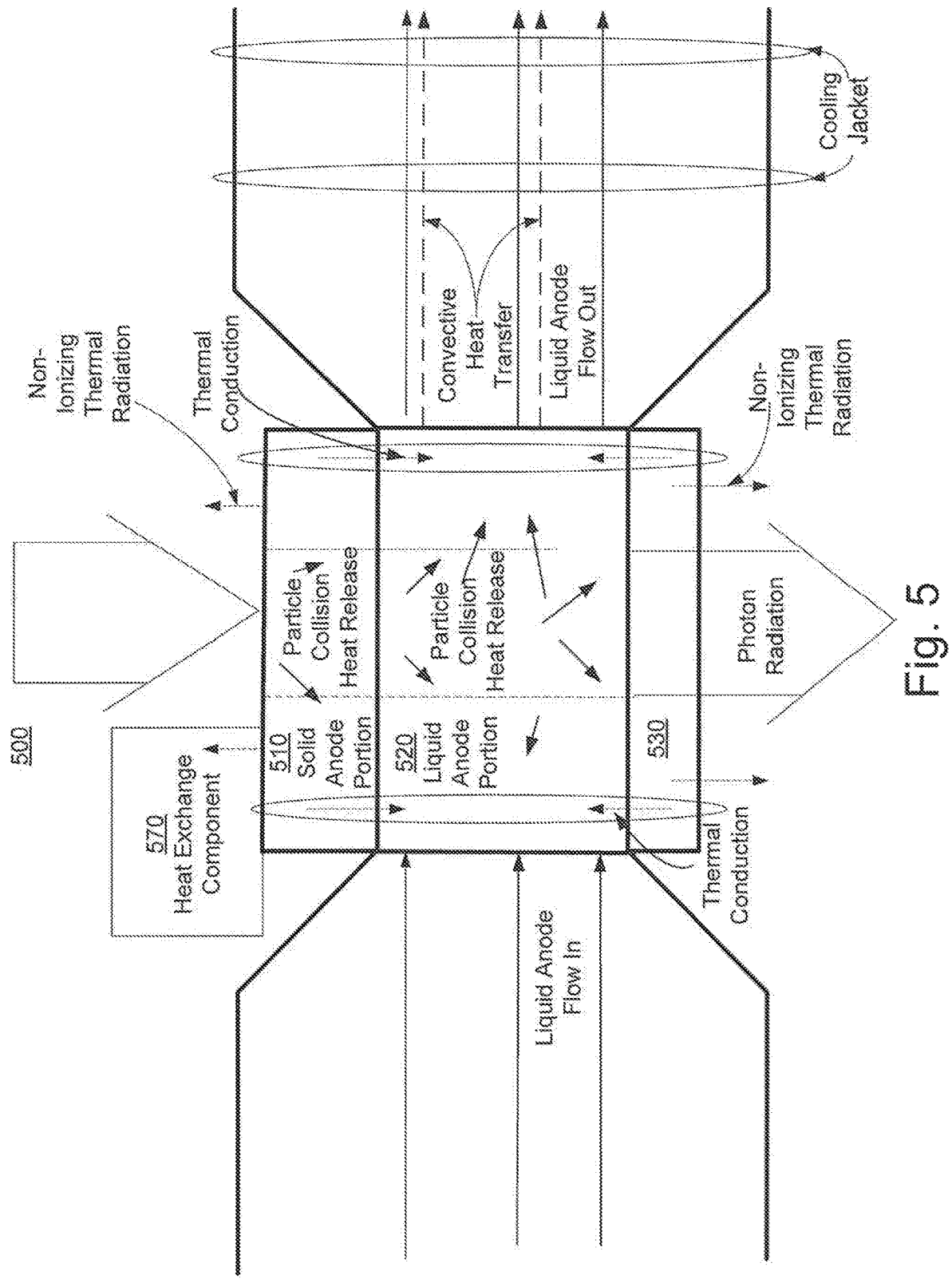
FIG. 5 is a block diagram of exemplary heat transfer in accordance with one embodiment

In some embodiments, the location of heat generation from particle collisions and the transfer of heat from the location of generation can impact the configuration of the HEDAT. FIG. 5 is a block diagram of an exemplary HEDAT 500 in accordance with one embodiment. In HEDAT 500, the particle collisions and heat generation occurs in the HEDAT-SAP 510, HEDAT-LAP 520, and solid window 530. The transfer of at least a portion of the resulting heat can occur through the removal of the heated liquid anode from the HEDAT-LAP 520 via the liquid anode flow. In some embodiments, the transfer of at least a portion of the resulting heat occurs through convective heat transfer via the liquid anode in HEDAT-LAP 520. In one exemplary embodiment, HEDAT-SAP 510 and solid window 530 convey at least a portion of the heat via conduction to the liquid anode in HEDAT-LAP 520 (e.g., internally within the HEDAT 500, etc), and also externally to the environment through non-ionizing thermal radiation. It is appreciated that the HEDAT-SAP 510 and solid window 530 can also include other heat removal components (e.g., radiator, coil, fan, etc.) that participate in heat transfer. In one exemplary embodiment, the HEDAT-SAP 510 is coupled to a heat exchange component 570. The heat exchange component 570 can enhance or supplement the heat removal by the liquid anode via various additional passive and active heat transfer mechanisms (e.g., radiator, coil, fan, etc.).

In some embodiments, molten metal is used as the liquid anode material. The liquid anode material is heated to at least the minimum melting temperature during idle times (e.g., an electron gun not actively generating an electron beam, system not generating radiation beams, etc.). When the radiation generation system is actively producing radiation beams and the liquid anode temperature increases in the HEDAT, the liquid anode material can be re-circulated and cooled down to a lower temperature but still hot enough to maintain a liquid state. In some embodiments, the molten metal liquid anode has a low melting temperature as reasonably or practically possible so that the flow can be more easily maintained during system idle while limiting absolute temperatures of the circulation system (e.g., tube walls, channel walls, etc.) during system operations.

Figure 6:
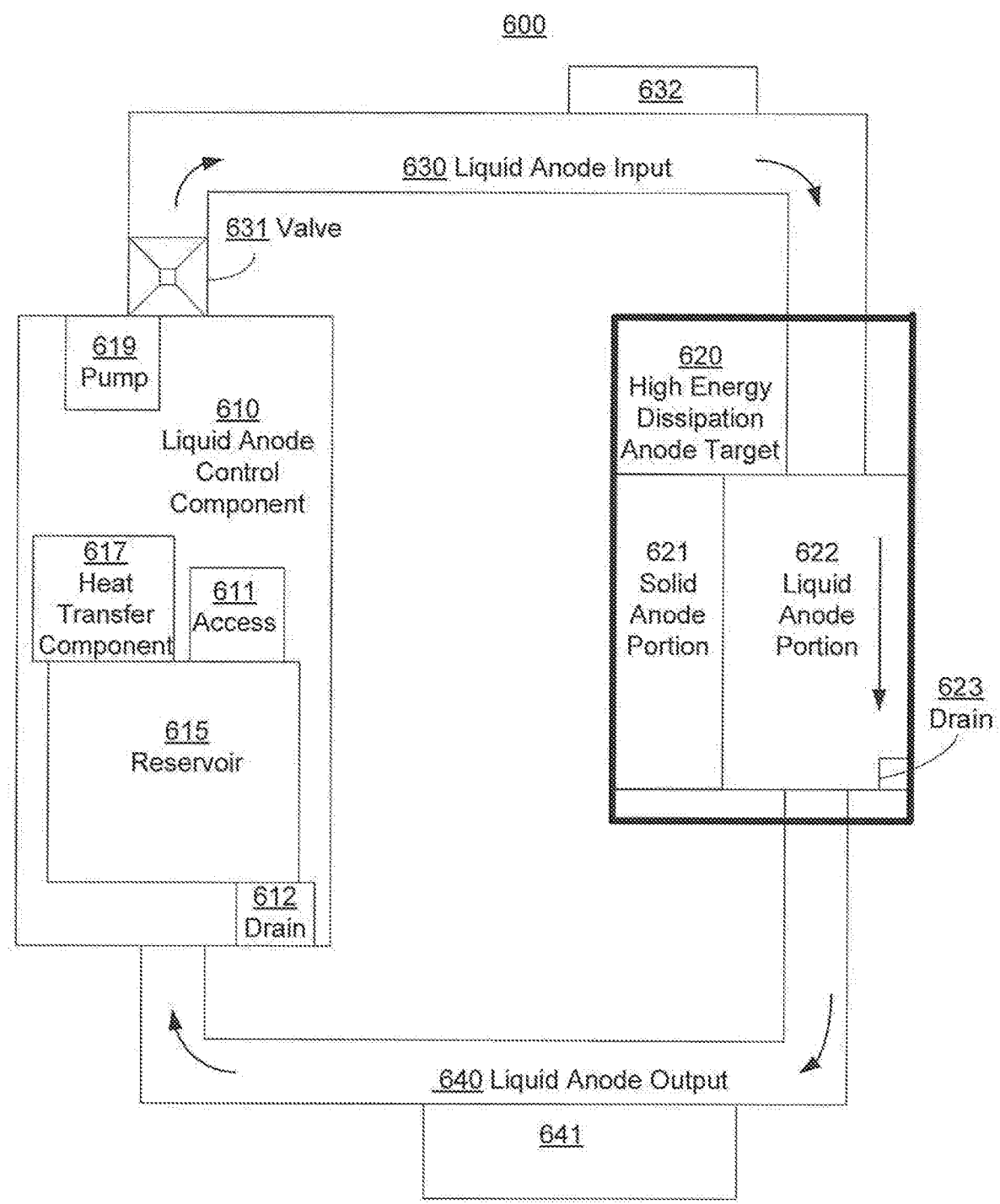
FIG. 6 is a block diagram of a different exemplary HEDAT-LAP flow system in accordance with one embodiment.

FIG. 6 is a block diagram of an exemplary liquid anode circulation system 600 in accordance with one embodiment. Liquid anode circulation system 600 includes liquid anode control component 610, HEDAT 620, liquid anode input component 630, and liquid anode output component 640. HEDAT 620 includes HEDAT-SAP 621 and HEDAT-LAP 622. A liquid anode can flow from liquid anode control component 610 through liquid anode input component 630 to HEDAT-LAP 622. The flow can continue through HEDAT-LAP 622 to liquid anode output 640 and back to liquid anode control component 610. Liquid anode control component 610 can control various characteristics of the liquid anode as it leaves the liquid anode control component (e.g., the temperature, flow rate, pressure, selection of liquid anode components or elements, etc.). In some embodiments, there is a reservoir 615 of liquid anode material in the liquid anode control component 610 that is pre-heated to convert the anode material into a liquid at the appropriate temperature. The liquid anode control component 610 can also include a cooling component or system for cooling the returned liquid anode and also participate in maintaining the reservoir at an appropriate temperature. In some embodiments, the temperature of the liquid is maintained at a level that does not adversely impact the liquid or solid components (e.g., does not melt the solid component, vaporizes the anode material itself, causes too high a density change, etc.).

The components of liquid anode circulation system 600 cooperatively operate to move flow of the liquid anode through the system. Liquid anode input component 630 conveys the liquid anode from liquid anode control component 610 to HEDAT-LAP 622. Liquid anode output component 640 conveys the liquid anode from HEDAT-LAP 622 to liquid anode control component 610. In some embodiments, liquid anode output component 640 is considered a cooling jacket. Liquid anode circulation system 600 can include various other components that participate in liquid anode flow control. In some embodiments, liquid anode circulation system 600 can include components to control various aspects of the liquid anode, including components that control flow (e.g., pump 619, valve 631, etc), components to add or remove liquid anode from the system (e.g., access point 611, drain 612, drain 623, etc.), heat transfer components to remove or add heat (e.g., component 617, heater, cooler, coil, fan, etc.), and so on. The system can also include intermediate components (e.g., 632, 641, etc.) at various locations that perform several functions that impact the liquid anode (e.g., heat, pump, drain, etc.).

It is appreciated a HEDAT can have various different configurations. Some surfaces or walls of a HEDAT can be selected for radioactive emission characteristics and other surfaces or walls (e.g. side wall, surface portion not in the electron beam path, etc.) can be selected with an emphasis on increased heat conductivity characteristics. In some embodiments, a surface or wall can also be selected for radiation resistance or blocking ability (e.g., to facilitate containment of radiation from undesirable emission, etc.). In some embodiments, the solid anode components of the HEDAT have various characteristics including one or more of the following: a low atomic number, low density, high heat capacity, high thermal conductivity, high melting point, high boiling point, high electrical conductivity, high yield strength, physical properties relatively unaffected by radiation (radiation hard or Rad-hard), noncorrosive, and so on. The solid anodes can be configured with various materials (e.g., beryllium, titanium, carbon, etc.). In some embodiments, a solid anode has one or more of the following characteristics: a density less than or equal to 5 g/cm3, an atomic number less than or equal to 25, a heat capacity greater than or equal to 0.03 J/gC, a thermal conductivity greater than or equal to 4 W/(mK), a melting point greater than or equal to 1,000 C, a boiling point greater than or equal to 2000° C., yield strength greater than or equal to 200 MPa, and electric conductivity greater than or equal to 1.0 E+5. In some embodiments, solid and liquid anodes avoid or minimize the inclusion of lead and cadmium. In some embodiments, a liquid anode has one or more of the following characteristics: a density greater than or equal to 6 g/cm3, an atomic number greater than or equal to 30, a heat capacity greater than or equal to 0.03 J/gC, a thermal conductivity greater than or equal to 4.0 W/(mK), a melting point lower than or equal to 150° C., a boiling point greater than or equal to 2,000° C., and viscosity lower or equal to 0.02 Pa-s. FIG. 7 is a table of liquid anode elements in accordance with one exemplary embodiment. Several candidate low melting temperature metals and eutectics are listed in the table.

It is appreciated the configuration of HEDAT-SAP and HEDAT-LAP can be coordinated in accordance with various characteristics and objectives to achieve efficient generation of a radiation beam. In one embodiment, configuration of the HEDAT-SAP and HEDAT-LAP is selected based upon collaborative operation and corresponding impacts. In one exemplary implementation, the individual and collaborative impacts of the HEDAT-SAP and HEDAT-LAP characteristics on heat generation and heat dissipation are considered in the configuration selection.

In one embodiment, a HEDAT-SAP generates less heat than a typical conventional solid anode under exposure to similar relatively high energy levels. The HEDAT can rely on the HEDAT-LAP producing some or most of the radiation generation to meet desired radiation output, thus the HEDAT-SAP can be thinner than a typical conventional solid anode. In one exemplary implementation, the relatively high energy input particles can penetrate the HEDAT-SAP easier than a conventional solid anode with less generation of heat. Less generation of heat means less heat has to be dissipated by the HEDAT-SAP and the heat capacity of the HEDAT has a better opportunity to keep up with the heat generation without overheating. The liquid anode can flow though the HEDAT-LAP 1) allowing relatively cool liquid anode to flow in, 2) participate in particle collision and radiation generation in the HEDAT-LAP while absorbing corresponding energy and heat generation, and 3) allowing the relatively warm liquid anode to flow out without excessive heat build up or overheating. The liquid anode can also assist absorb heat transferred from the HEDAT-SAP and include the heat in the relatively warm liquid anode to flow out without excessive heat build up or overheating.

The HEDAT-SAP can be configured to assist control of the liquid anode flow. In some embodiments, the HEDAT-SAP is configured to restrict or confine the liquid anode flow to a prescribed area. In some embodiments, the confinement can cause compaction or compression of the liquid anode, which in turn can contribute to increased radiation emission. Different materials with different characteristics can be utilized in the different components of the HEDAT. Thus, coordinated configuration of the HEDAT-SAP and HEDAT-LAP facilitates enhanced performance.

It is appreciated the configuration within the HEDAT-LAP can also vary. A HEDAT-LAP can be configured with multiple liquid anode channels. In some embodiments, the liquid anode channels can offer improved fluid dynamics and/or the ability to operate at multiple energies. The liquid anode flow in the channels can be controlled (e.g., turned on, shut off, increased, decreased, etc.). Valves can be utilized to implement the control. The amount of flow can be based upon the beam energy. At lower energies less anode material is required to stop the incident electrons while at higher energies more anode material is required. Use of the channels can be helpful in maintaining a flow pattern and to reduce eddies or local recirculation within the HEDAT-LAP channel or chamber. The channels can contain different anode materials that help increase the flux while minimizing electron straggle. In one embodiment, a higher energy channel contains a higher Z liquid anode (e.g., like Fields' metal, etc.) and a low energy channel contains lower Z liquid anode (e.g., gallium, etc.).

Figure 8:
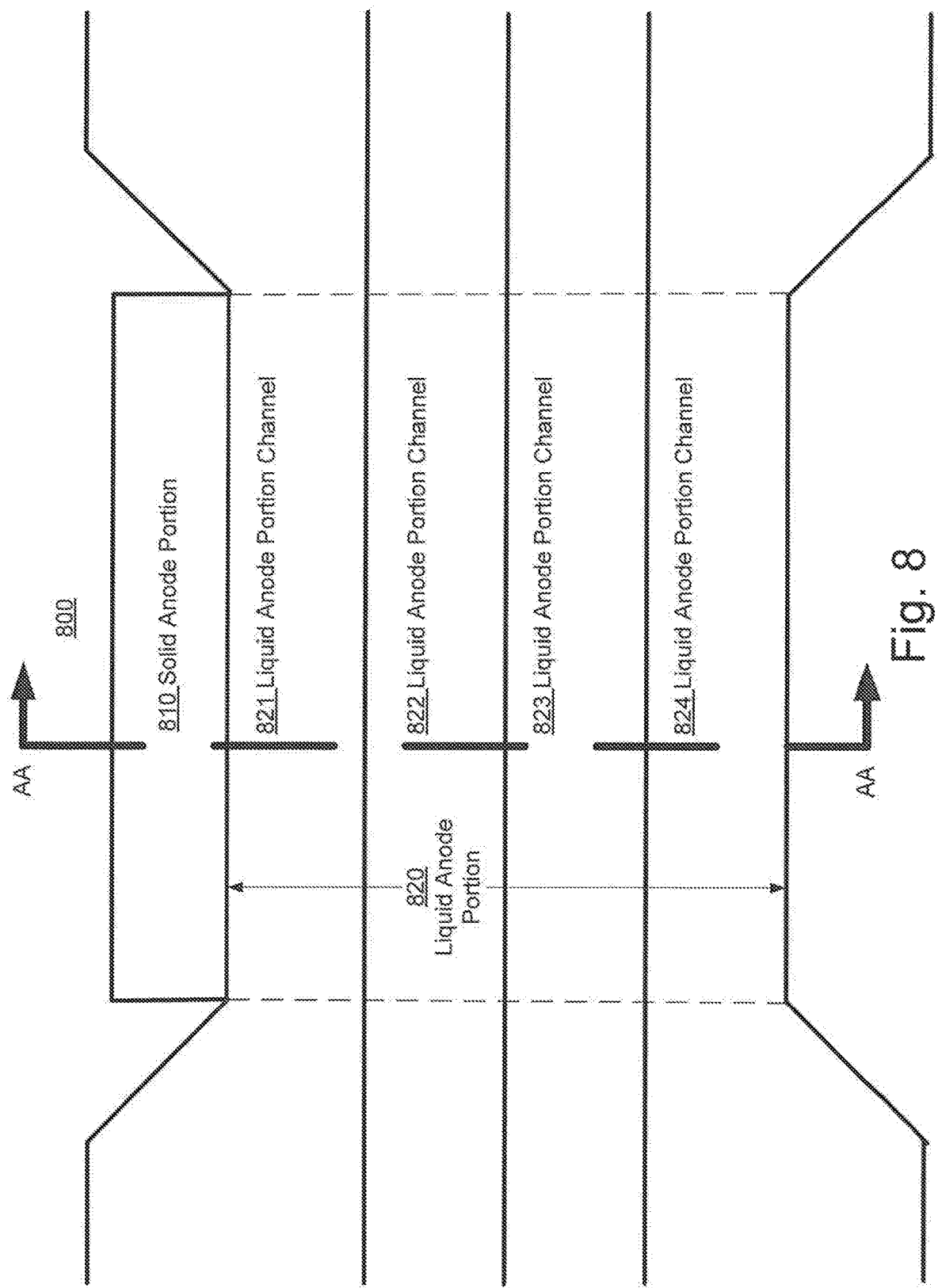
FIG. 8 is a block diagram of an exemplary HEDAT in accordance with one embodiment.

FIG. 8 is block diagram of exemplary HEDAT 800. HEDAT 800 includes HEDAT-SAP 810 and HEDAT-LAP 820. HEDAT-LAP 820 includes multiple HEDAT-LAP channels (e.g., 821, 822, 823, 824, etc.). The HEDAT-LAP channels can have different configurations and characteristics. The HEDAT-LAP channels can have the same or different liquid anode flows (e.g., same or different flow rate, pressure, temperature, direction, etc.). The liquid anode channels can convey different liquid anode material or components. The liquid anodes can have different characteristics (e.g., viscosity, corrosion, temperature conductivity, etc.). The multiple different liquid anodes can correspond to liquid anodes from the liquid anode table 700. In some embodiments, HEDAT-LAP channel 821 can include a field's metal alloy, the HEDAT-LAP channel 822 can include a wood's metal alloy, the HEDAT-LAP channel 823 can include a rose's metal alloy, and the HEDAT-LAP channel 821 can also include a field's metal alloy. It is appreciated that the material that forms the walls or components of the different liquid anode channels can vary.

In some embodiments, the configuration of the channel flow area dimensions and the walls that form them are the same. In another embodiment, the configuration of the channel flow area dimensions and the walls that form them vary. FIG. 9 is a block diagram of an exemplary side view of HEDAT 800 with different channel dimensions. The side view in FIG. 9 is through cut line AA of FIG. 8. The HEDAT-LAP channels (e.g., 821, 822, 823, 824, etc.) can have different dimensions. In some embodiments, the height and width dimensions of liquid anode channels 821 and 824 are the same, the height dimensions of liquid anode channel 822 and 823 are different than liquid anode channels 821 and 824, and the width dimension of liquid anode channel 823 is different than liquid anode channels 821, 822, and 824. The walls (e.g., 871, 872, 873, 874, 878, etc.) that form the HEDAT-LAP channels can have different dimensions. In some embodiments, the height and width dimensions of channel walls 872 and 874 are the same, the height dimension of channel wall 873 is different than channel wall 872 and 874, and the width dimension of channel walls 872 and 878 are different than 872 and 874. In some embodiments, a HEDAT-SAP (e.g., 871, 875, etc.) serve as channel walls or surfaces. It is also appreciated that an interior HEDAT-LAP channel wall (e.g., 872, 874, 877, 878, etc.) can include solid anode material and serve as both an anode and a channel wall.

Figure 10:
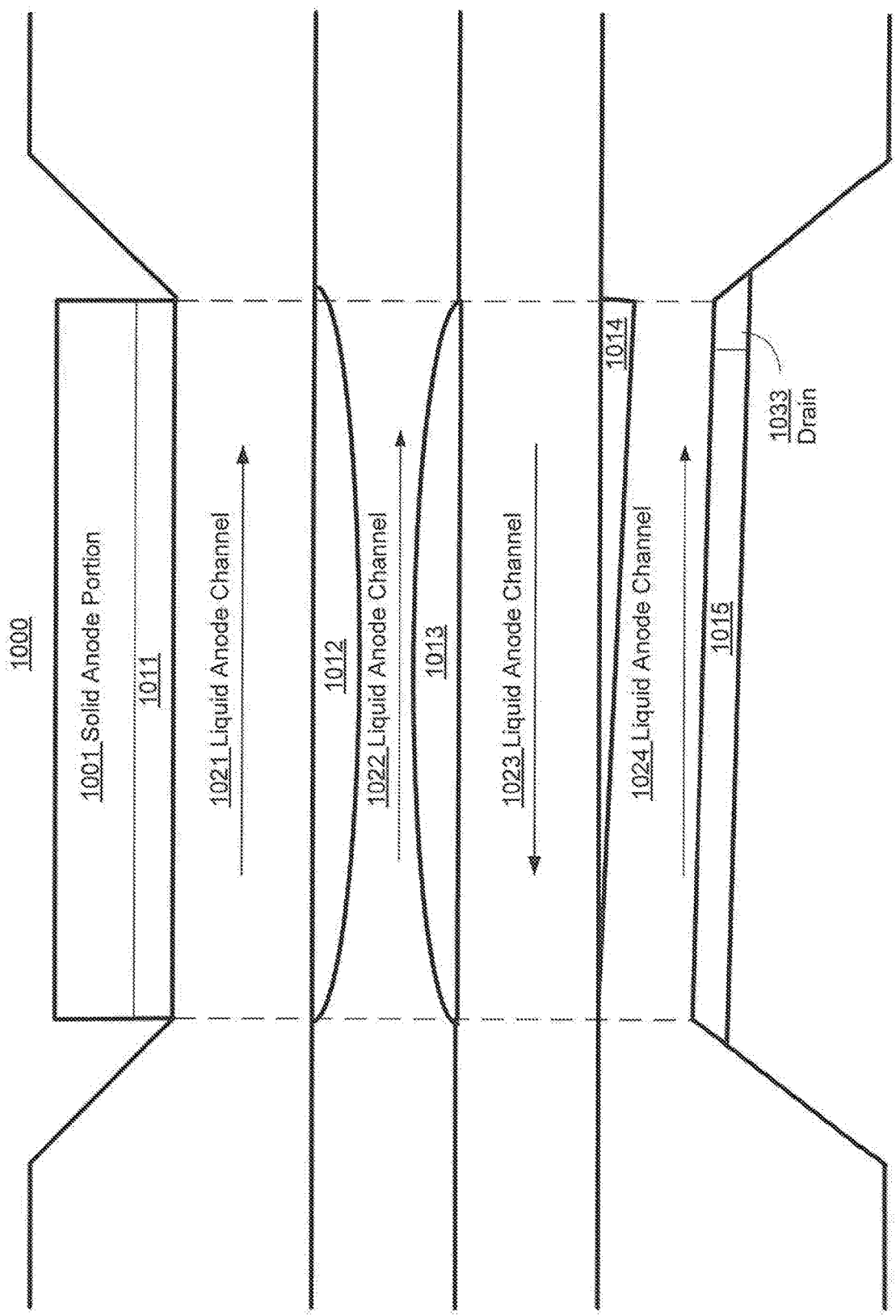
FIG. 10 is a block diagram of another exemplary HEDAT-LAP configuration in accordance with one embodiment.

FIG. 10 is an exemplary embodiment of another HEDAT-LAP 1000 configuration. HEDAT-LAP 1000 includes liquid anode channels 1021, 1022, 1023, and 1024 that are formed by channel walls 1011, 1012, 1013, 1014, and 1015. The shape of the channel walls 1011, 1012, 1013, 1014, and 1015 can be different. The shape of the channel wall can be configured to influence the liquid anode flow characteristics (e.g., increase or decrease flow rate, pressure, density, etc.). The liquid anode flow characteristics can in turn influence various factors or characteristics (e.g., the radiation generation, the temperature dissipation, etc.).

In some embodiments, a HEDAT enables increased controllability and performance over conventional liquid jet applications. The channel of a HEDAT-LAP confines a liquid anode to a more predictable behavior than an open jet streaming in a less confined space. The density of the liquid anode can be less in input/output components than a HEDAT-LAP to enable ease of flow to and from the liquid anode target. However, the flow can be changed in the HEDAT-LAP. In one exemplary embodiment, channel walls 1012 and 1013 can be utilized to impact the liquid anode flow characteristics (e.g., flow rate decreased, liquid compressed, density increased, etc.) to improve cooling and enable greater radiation generation. In some embodiments, the walls 1014 and 1015 are sloped to facilitate drainage of a liquid anode from the HEDAT-LAP. The liquid anode can be drained (e.g., via drain 1033, etc.) when not in use to prevent or minimize set up or solidification of the liquid anode in the HEDAT.

Figure 11:
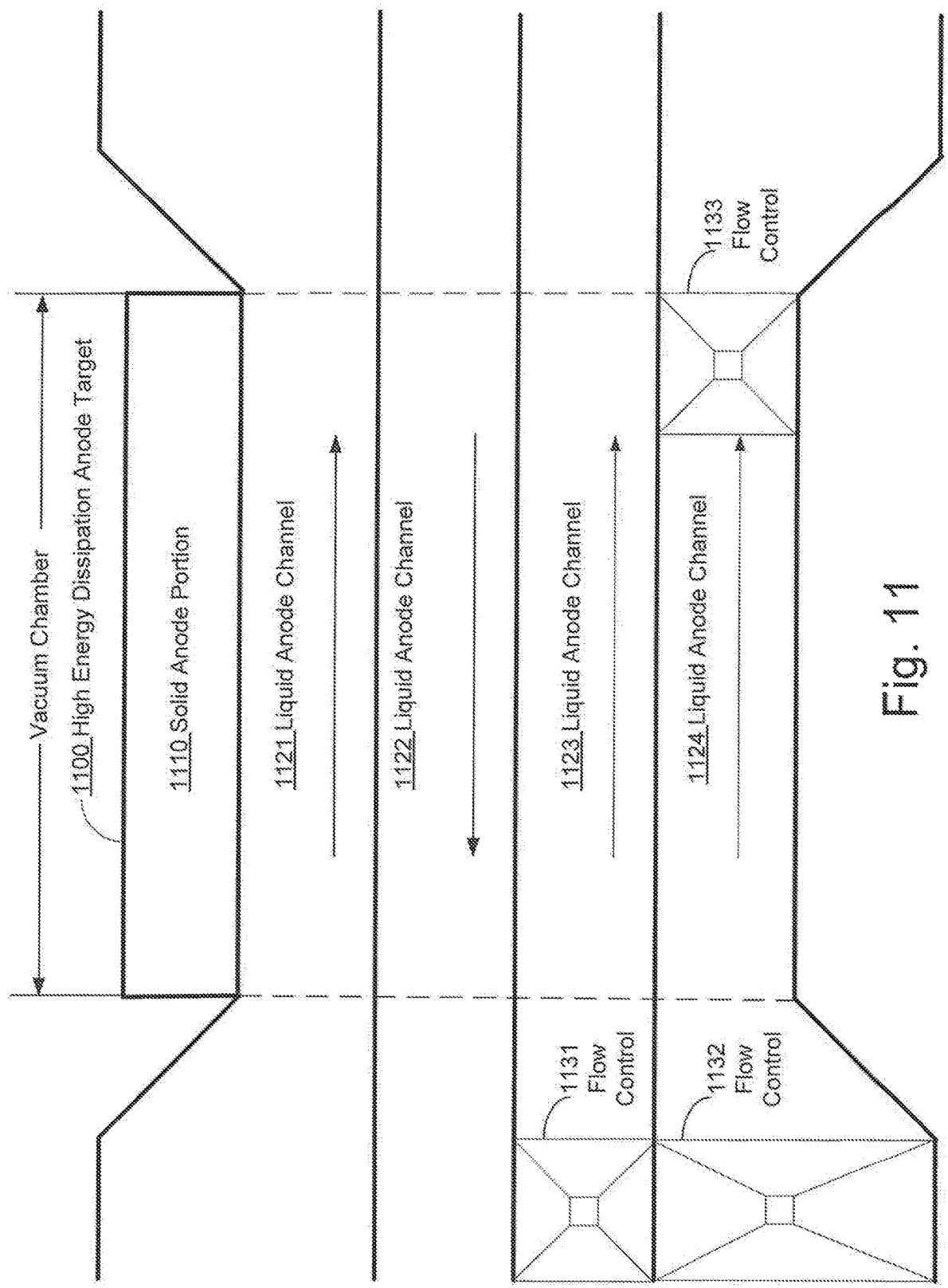
FIG. 11 is a block diagram of an exemplary HEDAT with auxiliary components in accordance with one embodiment.

It is appreciated that the flow in the channels can be configured and controlled separately. FIG. 11 is a block diagram of an exemplary embodiment of HEDAT 1100. The HEDAT 1100 includes liquid anode channels 1121, 1122, 1123, and 1124. The liquid anodes can flow in different directions in the liquid anode channels. The liquid anode flow in the channels can have individual controls (e.g., valves 1131, 1132, 1133, etc.).

It is appreciated that the configuration of the input and output components can include channels and the configuration of the channels and walls that form the channels can vary. In some embodiments, the configuration of the input and output components can include channels and walls that are similar to the configuration of the channels and walls within a HEDAT-LAP. In one exemplary implementation, a slip ring gantry is used and cooling liquid can be brought on and off the gantry via pathways that include a rotary joint.

FIG. 12 is a block diagram of an exemplary radiation generation method 1200.

In block 1210, an electron beam is received at a high energy dissipation anode target (HEDAT). In some embodiments, a high energy electron beam is received (e.g., greater than 1 MeV, etc.).

In block 1220, radiation is generated by collisions of the electron beam particles in with components of the HEDAT. In some embodiments, the radiation is generated by collisions of the electron beam particles with both a HEDAT-SAP and a HEDAT-LAP included in the high energy dissipation target. Energy resulting from electron beam collisions is absorbed by the HEDAT-SAP and the HEDAT-LAP.

In block 1230, heat resulting from energy absorption in the HEDAT-SAP and the HEDAT-LAP is dissipated. In some embodiments, a portion of the heat generated in the solid anode is dissipated by a liquid anode flow in the HEDAT-LAP.

In block 1240, flow of a liquid anode material to and from the HEDAT-LAP is controlled. In some embodiments, the temperature of the liquid anode is controlled.

In some embodiments, the flow rate is sufficiently high so that the required beam power can be absorbed without causing a temperature rise that melts the walls of the chamber containing the anode material itself, vaporize the anode material itself, or cause too high a density change. In an exemplary embodiment, Field's metal has density of approximately 7.9 gm/cc and a heat capacity of 285 J/kg. Thus, in order to limit the temperature rise to +100 deg X, the flow rate should be greater than approximately 44.4 cc/s per kW delivered to a target. To deliver 20 kW the flow rate should be about 88 cc/sec (approximately 6 Tbsp/sec).

In some embodiments, a HEDAT is compatible with precision controllability of the radiation beam. In some embodiments, a HEDAT facilitates generation and control of a relatively small diameter or circumference radiation beam. In some embodiments, radiation generation control facilitates ultra high radiation dose rates with high fidelity delivery. The systems and methods can be compatible with pulse width modulation and timing control resolution is configured to facilitate delivery fidelity approaching intra-pulse and micro-bunch levels (e.g., corresponding to individual bunches per radio frequency cycle in a pulse width, etc.). The radio frequency can be in the microwave range. The systems and methods are also compatible with multiple field treatment approaches and can enable dose delivery for each fraction/field to be effectively controlled. A HEDAT system can be implemented in systems running at power levels greater than 1.5 kW.

It is appreciated that a high energy dissipation target (HEDT) has been described with respect to a radiation generation target such as an anode. It is appreciated a HEDT can be utilized with various other applications in which a target is subjected to high energy beams. In some embodiments, the HEDAT is included in a monitor component. The monitor component can measure and track beam current and beam charge, which are used to draw a correlation with the dose rate and dose amount respectively.

Thus, the presented systems and methods facilitate efficient and effective radiation beam generation. In some embodiments, a HEDAT system and method enables improved performance at higher energy levels over limited traditional anode target approaches. The configuration selection of the solid portion and liquid portion of the HEDAT enables changes and improvements over conventional approaches, including operating at higher energy, dissipating great heat emission, and so on. In some embodiments, X-ray fluences can be increased by at least an order of magnitude over conventional levels. In some embodiments, a radiation system including a HEDAT produces intrinsic beam fluences with comparable or better spectral quality as those produced by a conventional slid only anode target. A HEDAT configuration can also facilitate better resolution and decreased treatment spot sizes. In some embodiments, a radiation system comprising a HEDAT configuration facilitates small focal spots for new and current treatments. The HEDAT system configuration can facilitate sharper edge definition during treatment.

It is appreciated that HEDAT configurations can be utilized in applications other that medical radiation applications. In some embodiments, HEDAT configurations can be utilized in various applications (e.g., medical, industrial, security, etc.). The HEDAT configuration can facilitate improved (e.g., faster, better image resolution, etc.) scanning of enclosed containers (e.g., packages, baggage, cargo scanning, etc.)

Some portions of the detailed descriptions are presented in terms of procedures, logic blocks, processing, and other symbolic representations of operations on data bits within a computer memory. These descriptions and representations are the means generally used by those skilled in data processing arts to effectively convey the substance of their work to others skilled in the art. A procedure, logic block, process, etc., is here, and generally, conceived to be a self-consistent sequence of steps or instructions leading to a desired result. The steps include physical manipulations of physical quantities. Usually, though not necessarily, these quantities take the form of electrical, magnetic, optical, or quantum signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are associated with the appropriate physical quantities and are merely convenient labels applied to these quantities. Unless specifically stated otherwise as apparent from the following discussions, it is appreciated that throughout the present application, discussions utilizing terms such as "processing", "computing", "calculating", "determining", "displaying" or the like, refer to the action and processes of a computer system, or similar processing device (e.g., an electrical, optical or quantum computing device) that manipulates and transforms data represented as physical (e.g., electronic) quantities. The terms refer to actions and processes of the processing devices that manipulate or transform physical quantities within a computer system's component (e.g., registers, memories, other such information storage, transmission or display devices, etc.) into other data similarly represented as physical quantities within other components.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as suited to the particular use contemplated. It is intended that the scope of the invention be defined by the Claims appended hereto and their equivalents. The listing of steps within method claims do not imply any particular order to performing the steps, unless explicitly stated in the claim.

What is claimed:

1. A therapeutic radiation generation system comprising:
a particle beam gun that generates an electron beam;
a high energy dissipation anode target (HEDAT), configured to receive the electron beam, absorb energy from the electron beam, generate a radiation beam, and dissipate heat, wherein the (HEDAT) includes a plurality of channels; and
a liquid anode control component configured to control a flow of a liquid anode to the HEDAT.

2. The therapeutic radiation generation system of claim 1, wherein the plurality of channels are configured to accommodate a plurality of liquid anode flows.

3. The therapeutic radiation generation system of claim 2, wherein a first one of the plurality of channels is configured to accommodate a first liquid anode flow and a second one of the plurality of channels is configured to accommodate a second liquid anode flow.

4. The therapeutic radiation generation system of claim 2, wherein the first liquid anode flow and the second liquid anode flow are different.

5. The therapeutic radiation generation system of claim 2, wherein configuration of a first one of the plurality of channels is different than configuration of a second one of the plurality of channels.

6. The therapeutic radiation generation system of claim 2, wherein first configuration of a wall in a first one of the plurality of channels is different than a second configuration of a wall in a second one of the plurality of channels.

7. The therapeutic radiation generation system of claim 6, wherein a difference in the first configuration of the first one of the plurality of channels and the second configuration of the second one of the plurality of channels results in a difference of a first flow of a liquid anode in the first one of the plurality of channels and a second flow of a liquid anode.

8. The therapeutic radiation generation system of claim 2, wherein a first configuration of the first one of the plurality of channels and a second configuration of the second one of the plurality of channels are coordinated for impacts on radiation emission from the HEDAT.

9. The therapeutic radiation generation system of claim 1, wherein a first one of the plurality of channels includes a first liquid anode and a second one of the plurality of channels includes a second liquid anode, wherein the first liquid anode is different than the second liquid anode.

10. A radiation method comprising:
receiving an electron beam at a high energy dissipation anode target (HEDAT);
absorbing energy from collisions of the electron beam with a wall of a channel and collisions of the electron beam with liquid anode contents in a plurality of channels in the HEDAT;
generating radiation based upon the energy absorption; and
dissipating heat resulting from energy absorption.

11. The radiation method of claim 10, further comprising:
controlling flow of a first liquid anode through a first one of the plurality of channels; and
controlling flow of a second liquid anode through a second one of the plurality of channels.

12. The radiation method of claim 10, further comprising forwarding a radiation beam to a treatment target.

13. The radiation method of claim 12, further comprising controlling liquid anode flows in the respective plurality of channels.

14. The radiation method of claim 13, wherein controlling the liquid anode flows includes adjusting the liquid anode flows based on resulting impacts to characteristics of the radiation beam.

15. A radiation therapy system comprising:
- a beam generation system that generates and transports a radiation beam in accordance with a prescribed treatment plan, where the beam generation system includes:
- a particle beam gun that generates a particle beam;
- a high energy dissipation anode target (HEDAT), configured to receive the electron beam, absorb energy from the electron beam, generate a radiation beam, and dissipate heat, wherein the (HEDAT) includes a channel configured to accommodate a liquid anode and a portion of a wall of the channel includes a solid anode; and
- a liquid anode control component configured to control a flow of the liquid anode.

16. The radiation therapy system of claim 15, wherein walls of the channel are configured to cause compress of the liquid anode in a manner that contributes to increased radiation emission.

17. The radiation therapy system of claim 15, wherein walls of the channel are configured to maintain a flow pattern and reduce local recirculation eddies.

18. The radiation therapy system of claim 15, wherein walls of the channel are configured to impact the flow of the liquid anode.

19. The radiation therapy system of claim 15, wherein the channel includes a solid anode portion (HEDAT-SAP) and a liquid anode portion (HEDAT-LAP).

20. The radiation therapy system of claim 15, wherein the HEDAT-SAP and HEDAT-LAP cooperatively operate to enhance energy compatibility characteristics of the HEDAT.

* * * * *